(12) United States Patent
Bergeron et al.

(10) Patent No.: US 7,465,295 B2
(45) Date of Patent: Dec. 16, 2008

(54) APPLICATOR FOR THE DELIVERY OF TOPICAL FORMULATIONS INTO MUCOSAL CAVITIES

(76) Inventors: Michel G. Bergeron, 1145 avenue des Erables, Quebec (CA) G1B 2N4; Andrew Desormeaux, 7640 de Beauchastel, Quebec (CA) G2C 1Y1; Rabeea F. Omar, 3035 de la Forest #24, Sainte-Foy, Quebec (CA) G1W 1L6

( * ) Notice: Subject to any disclaimer, the term of this patent is extended or adjusted under 35 U.S.C. 154(b) by 585 days.

(21) Appl. No.: 10/190,393

(22) Filed: Jul. 5, 2002

(65) Prior Publication Data

US 2003/0088217 A1 May 8, 2003

Related U.S. Application Data

(63) Continuation-in-part of application No. 09/693,289, filed on Oct. 20, 2000, now Pat. No. 6,500,460.

(51) Int. Cl.
*A61M 31/00* (2006.01)
(52) U.S. Cl. ...................................... 604/279
(58) Field of Classification Search .............. 604/15, 604/285, 286, 279, 264, 239, 275, 187, 212, 604/218, 240, 276, 228, 91, 226, 223, 244, 604/86
See application file for complete search history.

(56) References Cited

U.S. PATENT DOCUMENTS

| | | | |
|---|---|---|---|
| 2,683,456 A | | 7/1954 | Pierson |
| 4,636,202 A | * | 1/1987 | Lowin et al. ............ 604/236 |
| 4,846,801 A | * | 7/1989 | Okuda et al. ............ 604/218 |
| 4,980,152 A | | 12/1990 | Frazier et al. |
| 4,991,777 A | | 2/1991 | Sato |
| 5,057,310 A | | 10/1991 | Hill et al. |

(Continued)

FOREIGN PATENT DOCUMENTS

CN 2171372 7/1994

(Continued)

OTHER PUBLICATIONS

Piret, et al., Abstracts of the Interscience Conference on Antimicrobial Agents and Chemotherapy, vol. 38, p. 317.

(Continued)

*Primary Examiner*—Nicholas D. Lucchesi
*Assistant Examiner*—Christopher D Koharski
(74) *Attorney, Agent, or Firm*—Nicholas A. Kees; Godfrey & Kahn, S.C.

(57) ABSTRACT

This invention relates to a vaginal/ano-rectal applicator for the uniform delivery of any topical formulations to treat and/or prevent any infection and/or abnormal conditions of mucosa cavity caused by any pathogen and/or disease. The present applicator comprises a longitudinally extending body that has proximal and distal ends. The proximal end is located close to the external site of a mucosal cavity accessible to a user. The body has external perforations, made as a series of slots or holes, for uniform distribution of any formulation to be delivered to the user's mucosal cavity. Upon insertion of the applicator and expulsion of the formulation in the mucosal cavity, the formulation, which is contained in a reservoir, travels through a diffusion channel having a small volume, prior to being expelled through the perforations.

16 Claims, 5 Drawing Sheets

U.S. PATENT DOCUMENTS

| | | | |
|---|---|---|---|
| 5,098,711 A | | 3/1992 | Hill et al. |
| 5,125,914 A | | 6/1992 | Bassin |
| 5,167,646 A | * | 12/1992 | Swafford ................. 604/275 |
| 5,185,153 A | | 2/1993 | Pollock |
| 5,219,448 A | * | 6/1993 | Hackmann ................ 401/176 |
| 5,275,805 A | | 1/1994 | Nabi et al. |
| 5,275,806 A | | 1/1994 | Gbogi |
| 5,288,503 A | | 2/1994 | Wood et al. |
| 5,298,260 A | | 3/1994 | Viegas et al. |
| 5,424,060 A | | 6/1995 | Hauschild |
| 5,593,683 A | | 1/1997 | Viegas et al. |
| 5,609,581 A | * | 3/1997 | Fletcher et al. ............ 604/212 |
| 5,624,906 A | | 4/1997 | Vermeer |
| 5,633,349 A | | 5/1997 | Reichl |
| 5,668,170 A | | 9/1997 | Gyory |
| 5,674,511 A | | 10/1997 | Karcher et al. |
| 5,843,043 A | * | 12/1998 | Markus ................... 604/239 |
| 5,843,471 A | | 12/1998 | Chaykin |
| 5,857,991 A | | 1/1999 | Grothoff et al. |
| 5,908,612 A | | 6/1999 | Dailey et al. |
| 6,019,743 A | * | 2/2000 | Cole et al. ................. 604/15 |
| 6,203,803 B1 | | 3/2001 | De La Charriere et al. |
| 2001/0012857 A1 | | 8/2001 | Ognyanov et al. |
| 2003/0050224 A1 | | 3/2003 | Nedegaard |

FOREIGN PATENT DOCUMENTS

| | | | |
|---|---|---|---|
| DE | | 0139855 | 5/1985 |
| DE | | 3513645 | 10/1986 |
| DE | | 0761246 | 3/1997 |
| EP | | 0139855 | * 7/1984 |
| FR | | 2585575 | 2/1987 |
| GB | | 0386960 | 9/1990 |
| WO | | WO9300114 | 1/1993 |
| WO | | WO9742962 | 11/1997 |
| WO | | WO9944631 | 9/1999 |
| WO | | WO9953897 | 10/1999 |
| WO | | WO9953987 | 10/1999 |

OTHER PUBLICATIONS

Roddy, et al., N. Engl. J. Med. 1998, 339:504-510.

Howett, et al., Antimicrob. Agents Chemotherapy, Feb. 1999, 43(2):314-321.

Whittaker, C. et al., Appl. and Env. Microbio., 1994, vol. 48, No. 5, pp. 395-403.

Piret, et al., Abstracts of the Interscience Conference on Antimicrobial Agents and Chemotherapy, vol. 38, p. 317 published, Sep. 24, 1998.

* cited by examiner

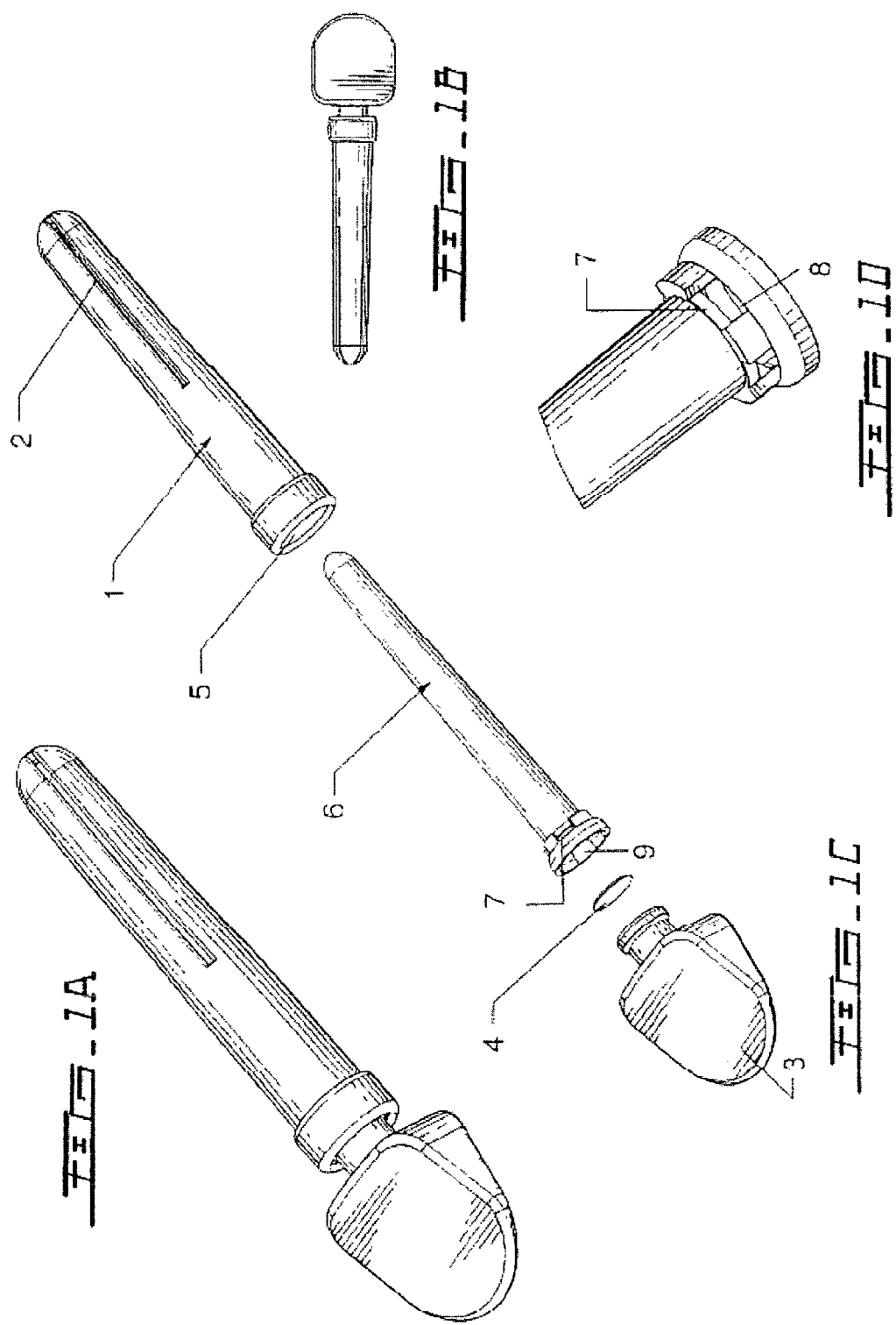

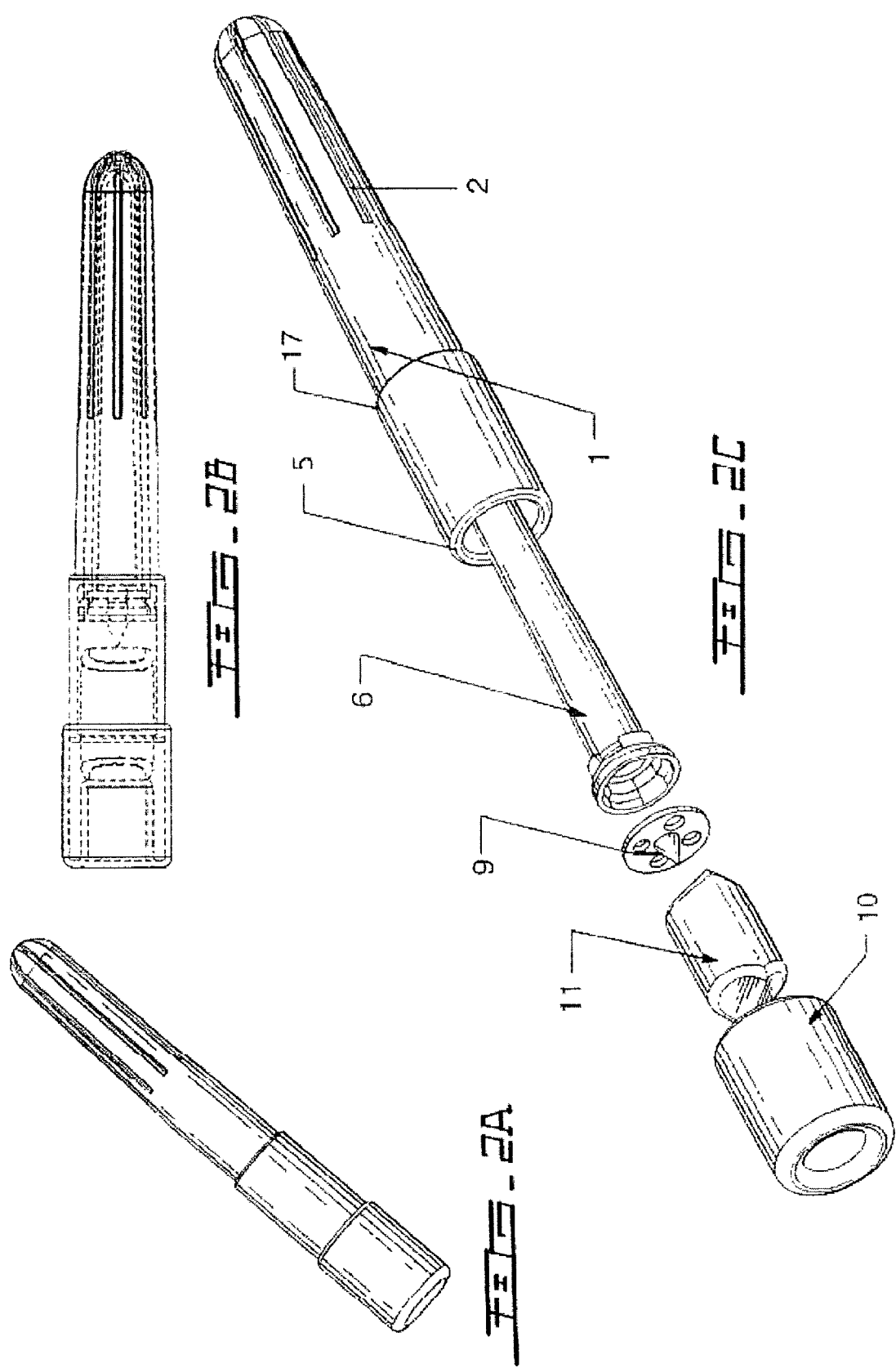

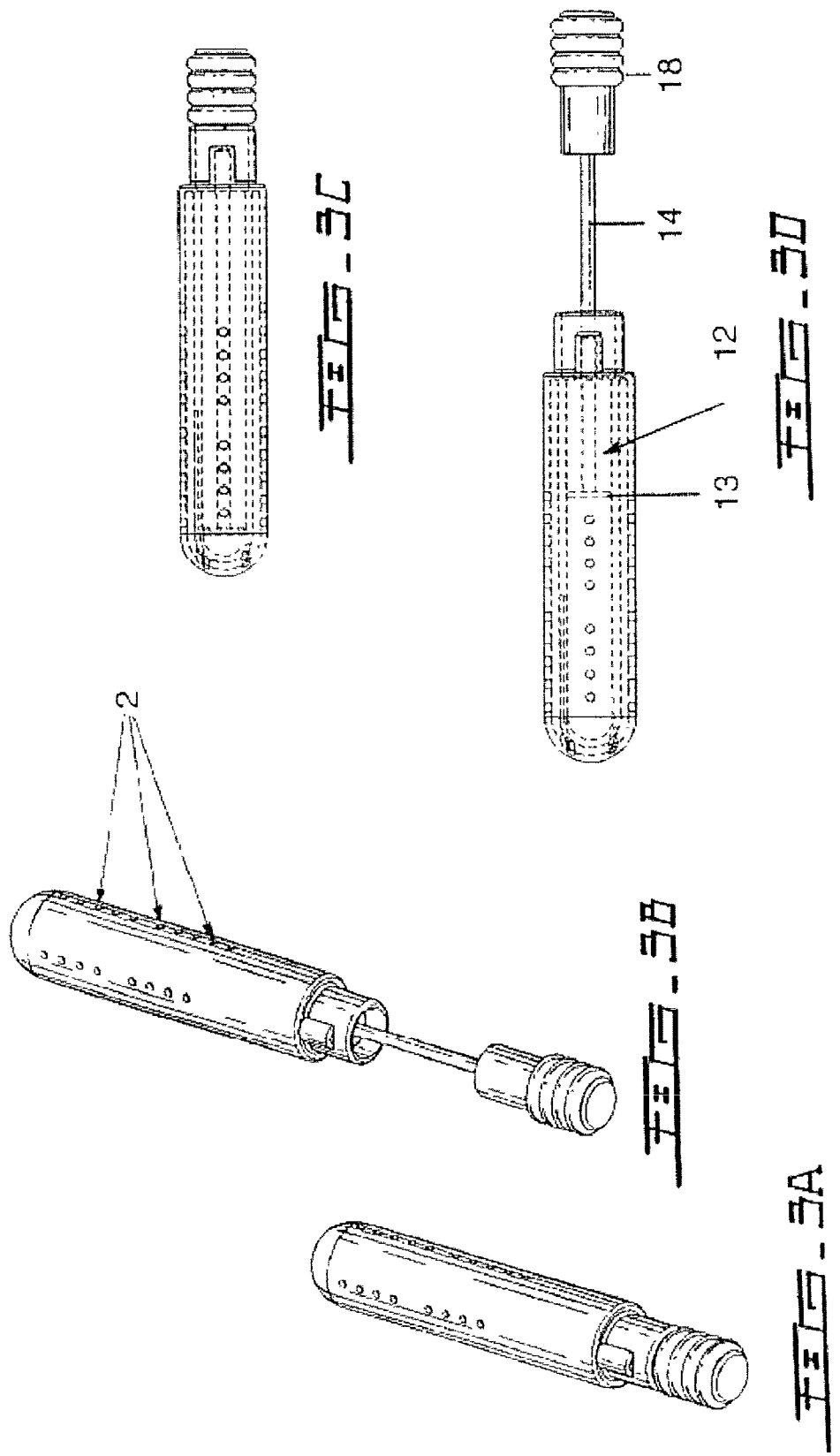

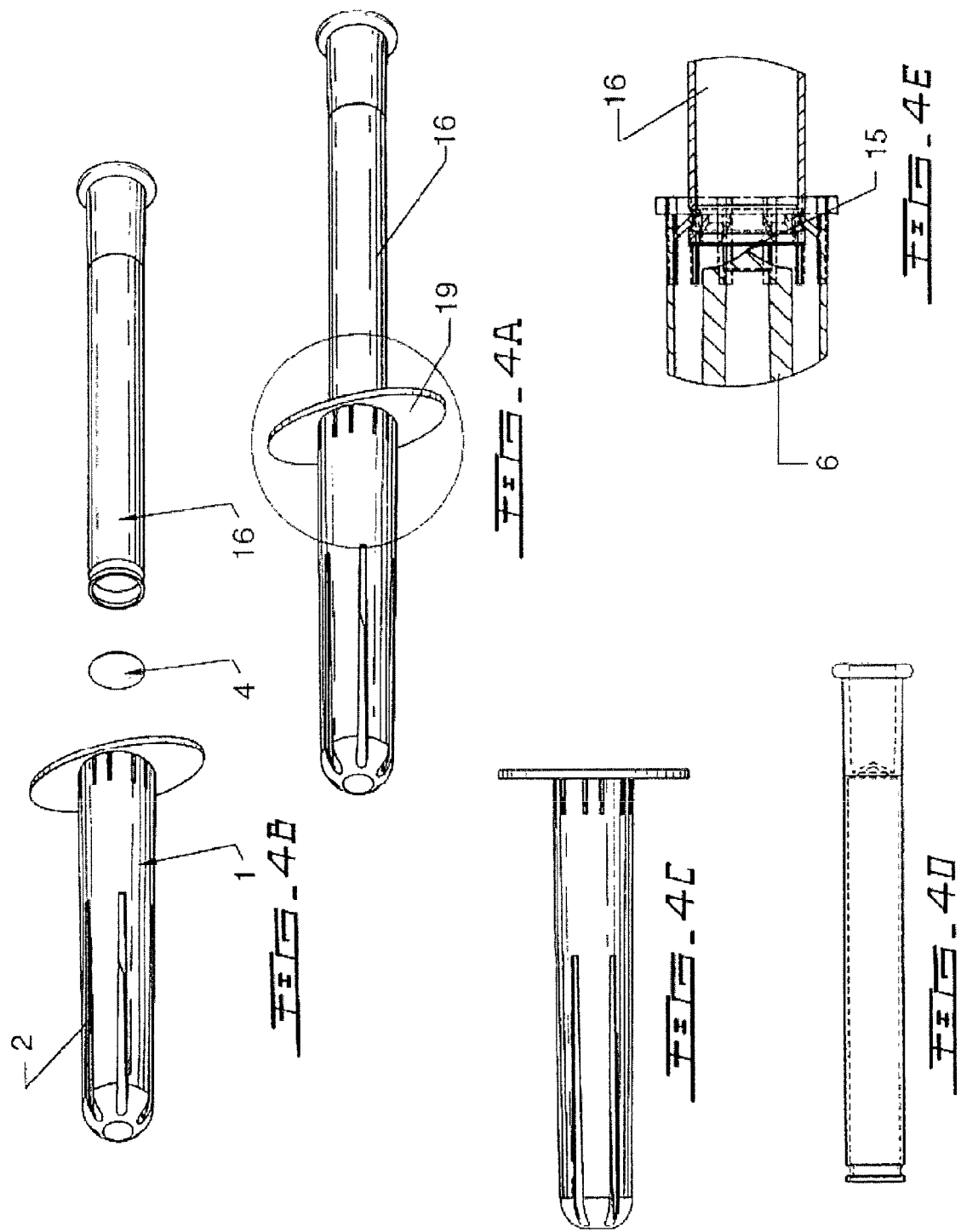

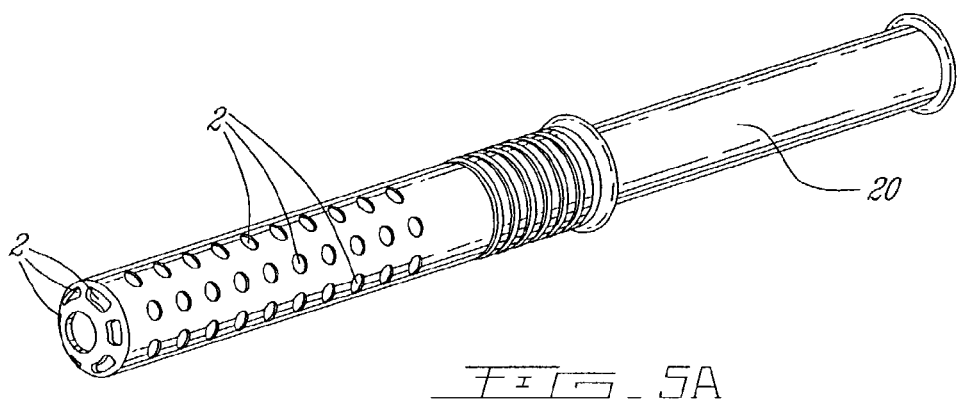
FIG_5A
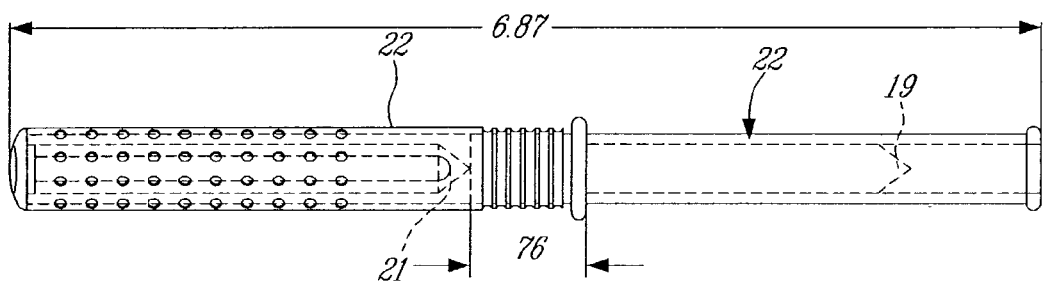
FIG_5B
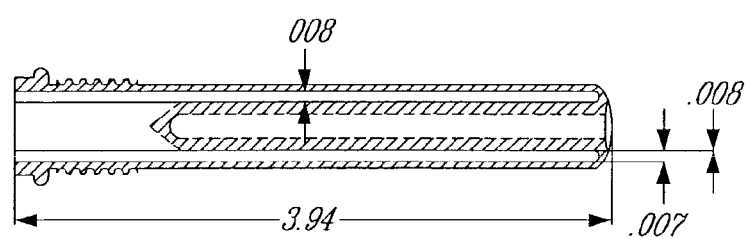
FIG_5C
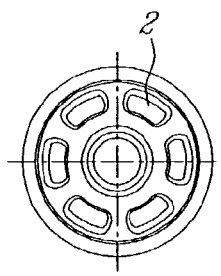
FIG_5D
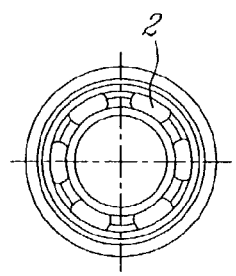
FIG_5E

APPLICATOR FOR THE DELIVERY OF TOPICAL FORMULATIONS INTO MUCOSAL CAVITIES

This application is a continuation-in-part of copending application Ser. No. 09/693,289 filed on Oct. 20, 2000 now U.S. Pat. No. 6,500,460.

FIELD OF THE INVENTION

This invention relates to the development of an applicator which allows uniform delivery of topical formulations to prevent or to treat any disease associated with or transmitted through mucosal cavities, or to prevent invasion by an external agent such as sperm or microbe.

BACKGROUND OF THE INVENTION

The efficacy of a topical formulation: a) to prevent or treat any disease/condition associated with or transmitted through mucosal cavities, b) to prevent invasion by an external agent such as sperm or microbe, or c) to deliver any drug, any vaccine, or any substance locally into the vagina and to the cervix area greatly depends on the ability to deliver the formulation uniformly throughout the entire mucosal cavity. For instance, the efficacy of a vaginal formulation to block the sexual transmission of pathogens causing sexually transmitted diseases (STDs) depends: i) on the nature of the formulation to be delivered and ii) on its ability to cover the entire vaginal/cervix area. However, the vaginal applicators currently available generally have a unique hole at the tip thereof so that their content is delivered mainly to the cervix area excluding the vagina, which results in a limited efficacy of vaginal formulations to protect against the transmission of pathogens causing STDs. There is thus a need for an applicator that provides uniform delivery of topical formulations to prevent or to treat any disease associated with or transmitted through mucosal cavities, or to prevent invasion by an external agent such as sperm or microbe. It appears from literature searches that there is no applicators or similar product on the market having such a design to allow delivery of their content to the entire vagina/cervix.

SUMMARY OF THE INVENTION

It is an object of the present invention to provide an applicator that can be used vaginally and/or ano-rectally to deliver topical formulations for treatment and/or prevention of infection and/or abnormal conditions of mucosae. The applicator can be designed in different ways to give the same required characteristics specified under detailed description of the invention. Examples of some different concepts are also discussed under the detailed description which are intended to describe some of the general design possibilities of the applicator, but are in no way intended to limit the scope thereof. It is important to mention that the final shape and appearance of the applicator can differ from the examples given herein.

It is also an objective of the invention to develop, for vaginal applications, an applicator which allows uniform distribution of the content to the entire vagina (delivery to sides) and cervix (delivery to front) for maximal protection against the sexual transmission of pathogens. Therefore, the present invention provides an applicator which allows about 360° distribution of its content into the vagina and far to the cervix which is a great improvement over existing conventional vaginal applicators which deliver contents only to front (cervix area only).

DESCRIPTION OF THE SPECIFIC EMBODIMENTS OF THE PRESENT INVENTION

This invention will be described hereinbelow by referring to specific embodiments and appended figures, which purpose is to illustrate the invention rather than to limit its scope.

BRIEF DESCRIPTION OF THE FIGURES

FIG. 1a is a perspective view illustrating a first embodiment of an applicator according to an aspect of the present invention.

FIG. 1b is a side elevational view showing typical dimensions in inches of the applicator of FIG. 1a.

FIG. 1c is an exploded view of the components of the applicator of FIG. 1a.

FIG. 1d is a perspective view illustrating the details of the external surface of the proximal end of the internal wall of the applicator of FIG. 1a.

FIG. 2a is a perspective view illustrating a second embodiment of an applicator according to an aspect of the present invention.

FIG. 2b is a side elevational view illustrating typical dimensions in inches of the applicator of FIG. 2a in both insertion position and actuated position.

FIG. 2c is an exploded view of the applicator of FIG. 2a.

FIG. 3a is a perspective view of a third embodiment of an applicator according to an aspect of the present invention; the applicator being shown in an insertion position.

FIG. 3b is a perspective view of the applicator of FIG. 3a shown in an actuated position.

FIG. 3c is a side elevational view illustrating the internal details of the applicator of FIG. 3a in the insertion position.

FIG. 3d is a side elevational view illustrating the internal details of the applicator of FIG. 3a in the actuated position.

FIG. 4a is a perspective view of a fourth embodiment of the applicator according to an aspect of the present invention.

FIG. 4b is an exploded view of the applicator of FIG. 4a.

FIG. 4c is a side elevational view of the external wall of the applicator of FIG. 4a where typical dimensions are given in inches.

FIG. 4d is a side elevational view of the piston/reservoir of the applicator of FIG. 4a where typical dimensions are given in inches.

FIG. 4e is a sectional side elevational view of a portion of the applicator of FIG. 4a illustrating the details of the arrangement of the piston/reservoir with regard to the internal and external walls of the body of the applicator.

FIG. 5a is a perspective view of a fifth embodiment of an applicator according to an aspect of the present invention; the applicator being shown in an uncompressed position.

FIG. 5b is a side elevational view illustrating the internal details of the applicator of FIG. 5a in the uncompressed position.

FIG. 5c is a side elevational view illustrating the internal details of the applicator of FIG. 5a in the insertion position.

FIG. 5d is a cross section of the distal end of the applicator of FIG. 5a from below.

FIG. 5e is a cross section of the proximal end of the applicator of FIG. 5a from above.

Design of Applicator for Vaginal/Ano-Rectal Delivery of Formulations

As mentioned above, the present invention provides an applicator which allows the uniform delivery of topical formulations to prevent or to treat any disease/condition associated with or transmitted through mucosal cavities, to prevent invasion by an external agent such as sperm or microbe, or to deliver any drug, any vaccine, or any substance locally into the vagina and to the cervix area. Before describing the applicator according to the present invention, a summary of the different characteristics such a device is required to possess is now presented (see also Table 1):

a) Uniform Distribution of Topical Formulations as Gel, Cream, Ointment, Liquid, Semi-Viscous, or any Film-Forming Component to the Entire Vagina/Cervix The applicator must deliver the formulation uniformly and must cover the whole vagina/cervix area by delivering through apical and lateral holes. Furthermore, the applicator should deliver sufficient amount to cover both cervix and vagina. This will allow maximal protection of individuals against pathogens causing STDs.

b) Efficient and Rapid Delivery of its Content

Most existing vaginal applicators deliver only a fraction of its content limiting the efficacy of the formulation. Therefore, the applicator must deliver the quantity required for sufficient coverage of all target mucosae. This is achieved through the design of the reservoir and calculating the average force of the fingers pressing on it to release its content. The time of delivery will vary depending on whether the content is delivered as a liquid, semi-viscous or gel. However, the delivery of applicator's content must be rapid.

c) Resistance to Temperature Variations (−40° C. to 60° C.)

The applicator itself should resist temperature variations because storage and transport environments will vary greatly from one country to another. It should be designed so that the applicator and the formulation remain unchanged under temperature conditions ranging from −40° C. to 60° C.

d) Compatibility of the Polymer of the Applicator with the Gel

The polymer used for the development of the vaginal applicator should not affect the properties of any formulation (stability, viscosity parameters, tolerance, efficacy to block pathogens, etc.), whether it is a gel, cream, ointment, liquid, semi-viscous, or any film-forming component.

e) Ease of Sterilization

The applicator design and material must ensure that it can be sterilized using a suitable method and should not result in changes in the characteristics of it or its content.

f) No Leakage

The applicator must be leak-proof under storage and transport conditions. If boxes are stacked on top of each other, the applicator should not leak its content.

g) Ease of Manipulation and Insertion

The applicator must be user friendly, easy to manipulate and easy to insert without causing discomfort to its user. Furthermore, it should be appealing to users.

h) Resistance to Breakage to Expansion of Content and Vibrations

The applicator should resist breakage if it falls from the user's hand or when it is handled during transport. It should also resist expansion of its content. Furthermore, the applicator should be stable and resist to vibrations during transport.

i) Compatibility with Agents and/or Conditions Present in the Surrounding Environment The applicator should resist to the agents and/or various conditions present in the surrounding environment. For example, it should not be affected by vaginal acidic pH, vaginal discharges or other similar conditions.

TABLE 1

Desired functions and target values of the applicator

| No | Function | Description | Target value |
|---|---|---|---|
| 1 | Distributes formulation as liquid, semi-viscous, gel, cream, ointment or any film-forming component | Once introduced, proceed to expulsion and distribution of formulation | Applicator delivers formulation as liquid, semi-viscous, gel, cream, ointment or any film-forming component |
| 2 | Distributes formulation uniformly | Distributes formulation to cover the whole vagina/cervix | Distributes content over about 360° in the vagina and over about 360° in and around the cervix |
| 3 | Contains formulation as liquid, semi-viscous, gel, cream, ointment or any film-forming component | Applicator has reservoir (where applicable, filled reservoir can be sealed with membrane or cap ± membrane; membrane can be removable or can be pierced by an applicator pin) | Reservoir holds a quantity of about 3-5 ml of any formulation |
| 4 | Leak-proof | No leakage from package and after initial manipulation | 0 ml |
| 5 | Easy to manipulate | Applicator can be held easily and is user friendly | Favourable opinion of volunteers |
| 6 | Easy to insert | Applicator inserted without pain and minimal resistance | Average diameter of about 0.5 inch (12.5 mm) |
| 7 | Delivers to vagina/cervix | The applicator length allows it to reach cervix | Average length of about 4.0 inch (about 102 mm) including reservoir and holding |
| 8 | Resists to fall | The applicator should not | Fall of about 60 |

TABLE 1-continued

Desired functions and target values of the applicator

| No | Function | Description | Target value |
|---|---|---|---|
|  |  | break and content should not leak if it falls from user's hands | inches (1.5 m) |
| 9 | Resists to surrounding environmental conditions | The applicator should not be affected by its content, vaginal secretions or packaging material |  |
| 10 | Not toxic and does not affect surrounding environmental conditions | Does not affect the composition or quality of formulation; it should also not affect the surrounding environment (e.g. vaginal flora) |  |
| 11 | Resists to vibration during transport | The applicator and reservoir should not be damaged and should operate normally after transport |  |
| 12 | Be efficient | Be operational (delivers content and distributes evenly without failure) | Favourable opinion of volunteers |
| 13 | Delivers fast | Content is rapidly ejected from applicator | Few seconds |
| 14 | Resists to temperature variation | The applicator should not be affected by temperature variations | −40° C. to +60° C. |
| 15 | Can be rinsed under water | Can be rinsed if drops from user's hands |  |

The applicator according to the present invention will now be described by way of different embodiments thereof, which are intended to describe some of the general design possibilities of the applicator, but are in no way intended to limit the scope thereof. It is important to mention that the final shape of the applicator can differ from the examples given hereinbelow. It is deemed that such designs can be modified to suit ano-rectal application.

FIGS. 1-5 illustrate specific examples or embodiments of applicators according to the present invention.

The present applicator comprises a longitudinally extending body that has proximal and distal ends. The proximal end is located close to the external site of the mucosal cavity accessible to the user. The body has external perforations, made as a series of slots or holes, for uniform distribution of any formulation as described above to be delivered to the user's mucosal cavity.

Upon insertion of the applicator and expulsion of the formulation in the mucosal cavity, the formulation, which is contained in a reservoir, advantageously travels through a diffusion channel having a small volume, prior to being expelled through the perforations. Indeed, this allows both the rapid expulsion of the formulation and the minimization of the quantity of formulation left in the applicator after expulsion.

The diffusion channel is created by a free space between two walls defining the body. The first wall is an external wall of the body and includes apertures. The second, non-perforated, internal wall is provided inside the first wall to create the diffusion channel. The internal wall is so configured and sized that it can be slidably inserted into the first wall. Alternatively, the internal wall, sized to be smaller than the first one, may be integrally molded with the external wall of the body.

The internal wall has a proximal end, which is an inlet end for the formulation into the diffusion channel. A directing element may also be provided to direct the formulation into the inlet end of the diffusion channel. The directing element therefore prevents entry of the formulation into another compartment than the diffusion channel.

A reservoir capable of receiving the formulation is also part of the applicator. The reservoir can be located near the body of the applicator or inside the body. The reservoir is operatively connected to an expulsion element. The expulsion element is itself connected to the proximal end of the body through a connector element. The expulsion element is actuated by the user. Upon application of compression, pull or push movements, the expulsion element releases the content of the reservoir, which is contacted with the proximal entry end of the diffusion channel. The formulation therefore travels into the diffusion channel to the mucosal cavity, being expulsed through the perforations.

As mentioned herein above, the present applicator is designed to uniformly deliver any formulation as liquid, semi-viscous, gel, cream, ointment or any other film-forming component described herein above into a mucosal cavity, with the smallest residual amount thereof left within the applicator.

Turning now to FIGS. 1*a*-1*d* of the appended drawings, a first embodiment of an applicator according to the present invention will be described. FIG. 1*b* shows an exploded view thereof. The external wall (1) of the body of the applicator shows perforations (2) (only one shown) made as one single slot extending from one side of the body through the opposite side with no interruption at the distal end of the external wall (1). The longitudinal slot therefore defines lateral and distal perforations. In this embodiment, the reservoir and the expulsion element are one single element (3) made of a compressible material. The formulation is contained in the reservoir, which ejects its content by pressing it with fingers. The reservoir is terminated by a membrane of low resistance to compression (4). The reservoir being the expulsion element, it is connected to the proximal end of the body through a connector element (5) represented by a screwable or snap-in connector element. In this particular embodiment, the internal wall (6) of the body is provided as a separated element dimensioned to be smaller than the external wall. The proximal end of the internal wall terminates with a protruding collar that sits onto the connector element formed at the proximal end of the external wall. The proximal part of the internal wall comprises a closing element (7), which closes the internal lumen formed by the internal wall. The closing element may have the shape of a disc. Alternatively, the proximal end of the internal wall may be integrally molded with the latter to be simply closed. Concentric to this closing element, there is an open concentric element (8) located at the periphery of the closing element. These elements provide for a generally called directing element, which directs the formulation into the diffusion channel formed between the internal and the external walls and away from the internal surface of the internal wall (6). FIG. 1c also shows a tapered element (9), located at the centre of the directing means, provided to break the membrane (4) when adequate pressure is applied.

A second embodiment of an applicator according to the present invention is illustrated in FIG. 2. The same peripheral and internal walls as in FIG. 1 are used in this applicator. In this specific version, a plurality of slots regularly spaced from each other are provided in the external wall. Furthermore, the expulsion element and the reservoir are also one single element, and the expulsion element is not a compressible reservoir. It is rather a piston-like structure (10), which comprises the formulation provided in a pouch (11). In this embodiment, the connector element (5) is telescopically insertable in the piston-like structure (10). The pouch is made of a material of low resistance to compression. To break this membrane, a tapered element is provided at the proximal end of the internal wall. FIG. 2 shows this tapered element (9) as a disc provided with a pointed portion. The disc sits on the proximal end of the internal wall, the pointed portion facing the pouch (11). In use, the piston-like structure (10) is pressed by the user, the membrane is thus pierced by the pointed portion, and the formulation is thus forced through the diffusion channel, and expelled through the perforations.

FIG. 3 illustrates a third embodiment of an applicator according to the present invention. While the two previous embodiments show a reservoir located near the proximal end of the diffusion channel, this third embodiment shows a reservoir (12) provided away from the proximal end of the diffusion channel. In this case, a seat (13) located away from the reservoir is provided. The seat is operatively connected to the piston (14) located proximally to the reservoir (12). The user pulls the piston and therefore compresses the reservoir, the content of which is engaged into the proximal inlet end of the diffusion channel. The formulation is expulsed through perforations made in the external wall of the body of the applicator, shown in FIG. 3 as a plurality of holes (2). The holes are spaced in such a way that the formulation is uniformly distributed into the mucosal cavity. The holes are located in the longitudinal section of the external wall as well as to the distal end thereof. FIG. 3 further shows that the internal and external walls of the body of the applicator may be integrally formed. Alternatively, the internal wall may also take the shape of the one shown in FIGS. 1 and 2, without the need of a tapered element. The reservoir may include a membrane of low resistance to compression in such a way that, when compressed by the pull movement of the piston (14), the membrane breaks and discharges its content into the diffusion channel. In this embodiment of the applicator, the directing element is formed by the proximal entry end of the diffusion channel and a closing element located this time at the proximal end of the body (not shown).

FIG. 4 shows a fourth embodiment of an applicator according to the present invention. In this embodiment, the reservoir and the expulsion element are a single element. A membrane (4) of low resistance is located close to the proximal end of the body (1). The external wall of the applicator comprises slots that are made as a plurality of grooves. The internal wall (6) is integrally formed with the outer wall. The internal wall terminates at its proximal end with a tapered element (15). The reservoir/piston (16) has a diameter that is slightly larger than the external diameter of the internal wall, but smaller than the internal diameter of the external wall of the body of the applicator. In use, the reservoir is slidably engaged between the two walls, the membrane is pierced and its contents are forced in to the diffusion channel and in the perforations located on the sides and at the distal end of the external wall.

FIG. 5 illustrates a fifth embodiment of an applicator according to the present invention. The reservoir and the expulsion element are one single element (20). The reservoir is filled with a formulation and sealed with a material of low resistance such as a membrane for instance (not shown), which is easily pierced by a pin provided within the expulsion element or pealed off for example. The external wall of the applicator comprises holes (2) distributed substantially uniformly on the body of the applicator and at the tip thereof (see FIG. 5d). The internal wall may be either integrally formed with the external wall or assembled therewith, by insertion, by a push and snap movement, or by a push and screw movement. The proximal end of the internal wall may be shaped to comprise a pointed portion (21). Alternatively, the proximal end of the internal wall may be substantially flat but configured to receive a tapered element (of the type of the element 9 of FIG. 2c, without holes, for example). Ideally, the piston comprises a filled proximal portion (22), which is terminated at the proximal end thereof with a chevron-like tip (19) configured to complementarily fit with the shape and dimension of the pointed portion. Upon activation, the external wall of the reservoir piston engages the diffusion channel, the membrane is pierced or pealed off for example before assembly and the formulation is forced into the diffusion channel. Alternatively, the formulation can be provided as a separate pouch, which is put in place into the reservoir, instead of having a pre-filled piston. FIG. 5c shows the applicator after delivery of its formulation contents. Essentially, no or minimal formulation is lost in void volumes. There are no connecting elements per se in this embodiment, although the reservoir comes into connection with the diffusion channel at the proximal inlet thereof.

It is to be noted that in all the above described embodiments, the directing element may be integrally formed with the proximal end of the internal wall of the body or be provided as a closing element or disc to block the passage of the formulation into the internal lumen formed by the internal wall and to direct the flow of the formulation into the diffusion channel.

Further, for ease of use, grasping elements may be provided in some embodiments to help the user maintain the applicator in place while actuating the expulsion element. More specifically, in the second embodiment, the grasping element is defined by the annular collar (17) formed at the outer periphery of the connector element (5). The annular collar has an external thickness such that the user has enough space to grasp the distal end of the collar between fingers and push the piston with another finger. In the third embodiment, the grasping element is provided at the proximal end of the piston (see numeral 18). The external wall of the body being of a larger section than the piston, the user can hold the body of the applicator by its proximal end with one hand and push the piston with another. Finally, in the fourth embodiment, the grasping element is provided as an elliptic handle (19) located at the proximal end of the body of the applicator and surrounding the connector element. This handle may be held between two fingers, while the piston is pushed with another finger.

From the foregoing, people in the art will appreciate that the applicator according to the present invention allows for a deliver of a formulation from the very end thereof as well as from the sides thereof in such a way to cover the whole vagina/cervix, thus providing a maximal protection against pathogens causing STDs.

Additionally, it will be apparent that the applicator according to the present invention can be used for the delivery of any topical formulations used to cover cervical/vaginal/ano-rectal mucosae for the treatment and/or prevention of infection and/or abnormal conditions of mucosae. The applicator can also be used to deliver i) any topical formulations that can prevent the sexual transmission of pathogens causing STDs, ii) vaginal contraceptive formulations, iii) topical microbicidal formulations against specific diseases and iv) any antimicrobial, bactericidal, virucidal, chemotherapeutic, anti-inflammatory, antineoplastic, or immunomodulatory agent, detergents, microbial adsorption inhibitor, skin penetration enhancing agent, cytokine, antigen, vaccines, radioactive agents or combination of them thereof.

What is claimed is:

1. An applicator for delivering a formulation into a user's mucosal cavity comprising:
   a hollow cylindrical body having an open proximal end, a partially closed distal end, and a cylindrical wall extending longitudinally therebetween; said cylindrical wall being provided with a plurality of peripheral holes disposed both along its periphery and a major portion of its length;
   an internal wall structure secured to said partially closed distal end of said hollow cylindrical body end so as to extend generally coaxially therein for a major portion of the length thereof substantially overlapping with the length of said hollow cylindrical body having said peripheral holes disposed thereon; and
   a piston for reciprocal movement in said hollow cylindrical body having a proximal end, an open distal end and including an internal abutting wall defining a reservoir in said hollow piston for complementary cooperation with said internal wall structure;
   whereby, in operation, pushing said piston including the formulation in its reservoir in said hollow cylindrical body causes the reservoir to receive said internal wall structure therein via said piston open distal end causing the formulation to exit the reservoir and to subsequently exit through said plurality of peripheral holes along the length of said cylindrical body and said partially closed distal end, yielding a uniform delivery of the formulation within the mucosal cavity of the user.

2. An applicator as recited in claim 1, wherein said internal wall structure is cylindrical and said reservoir is cylindrical.

3. An applicator as recited in claim 1, wherein said internal wall structure is mounted to said partially closed distal end.

4. An applicator as recited in claim 1, wherein said plurality of peripheral holes are both longitudinally and radially spaced in such a way that the formulation is delivered substantially uniformly to the mucosal cavity.

5. An applicator as recited in claim 1, wherein said partially closed distal end of said hollow cylindrical body includes a series of tip holes symmetrically located near the periphery of said partially closed distal end.

6. An applicator as recited in claim 5, wherein a gap free of holes is provided between said plurality of peripheral holes and said partially closed distal end.

7. An applicator as recited in claim 1, wherein said reservoir is filled with the formulation, and said piston is then sealed at its distal end prior to operation.

8. An applicator as recited in claim 1, wherein said piston is sealed with a membrane that can be pealed off or pierced prior to operation.

9. An applicator as recited in claim 1, wherein said piston includes an annular collar near said proximal end thereof for abutment with said open proximal end of said hollow cylindrical body.

10. An applicator as recited in claim 1, wherein said hollow cylindrical body includes a grasping element on its cylindrical wall near said open proximal end.

11. An applicator as recited in claim 10, wherein said grasping element is in the form of a series of annular collars.

12. An applicator as recited in claim 1, wherein said internal wall structure is tubular.

13. An applicator as recited in claim 1, wherein said internal wall structure extends within said hollow cylindrical body for a length at least equal to the length of said hollow cylindrical body having said peripheral holes disposed thereon.

14. An applicator as recited in claim 1, wherein said formulation comprises a gel formulation.

15. An applicator as recited in claim 1, wherein said formulation comprises a liquid formulation.

16. An applicator as recited in claim 15, wherein said liquid formulation is a viscous liquid formulation.

* * * * *

UNITED STATES PATENT AND TRADEMARK OFFICE
CERTIFICATE OF CORRECTION

PATENT NO. : 7,465,295 B2  Page 1 of 1
APPLICATION NO. : 10/190393
DATED : December 16, 2008
INVENTOR(S) : Bergeron et al.

It is certified that error appears in the above-identified patent and that said Letters Patent is hereby corrected as shown below:

Title Page, Item (76) Inventors
The inventor name "Andrew" should be deleted and replaced with the name "André"

Signed and Sealed this

Tenth Day of March, 2009

JOHN DOLL
*Acting Director of the United States Patent and Trademark Office*